(12) United States Patent
Wu et al.

(10) Patent No.: US 11,925,457 B2
(45) Date of Patent: Mar. 12, 2024

(54) DEVICE FOR ENCOURAGING AND GUIDING A SPIROMETER USER AND ITS METHOD

(71) Applicants: Taichung Veterans General Hospital, Taichung (TW); Central Taiwan University of Science and Technology, Taichung (TW)

(72) Inventors: Ming-Feng Wu, Taichung (TW); Yu-Hsuan Chen, Taichung (TW); Kuo-Chih Su, Taichung (TW); Chun-Hsiang Wang, Taichung (TW)

(73) Assignees: TAICHUNG VETERANS GENERAL HOSPITAL, Taichung (TW); CENTRAL TAIWAN UNIVERSITY OF SCIENCE AND TECHNOLOGY, Taichung (TW)

( * ) Notice: Subject to any disclaimer, the term of this patent is extended or adjusted under 35 U.S.C. 154(b) by 441 days.

(21) Appl. No.: 17/177,321

(22) Filed: Feb. 17, 2021

(65) Prior Publication Data

US 2021/0251513 A1    Aug. 19, 2021

(30) Foreign Application Priority Data

Feb. 19, 2020  (TW) ................................. 109105251

(51) Int. Cl.
*A61B 5/097*    (2006.01)
*A61B 5/087*    (2006.01)

(52) U.S. Cl.
CPC ............ *A61B 5/097* (2013.01); *A61B 5/0875* (2013.01)

(58) Field of Classification Search
CPC ....... A61B 5/097; A61B 5/0875; A61B 5/087; A61B 5/091; A61B 5/0871
See application file for complete search history.

(56) References Cited

U.S. PATENT DOCUMENTS

2019/0053769 A1*  2/2019  O'Keeffe ........... A63B 71/0622
2021/0001169 A1*  1/2021  Roussel ............. A63B 24/0062

FOREIGN PATENT DOCUMENTS

| CN | 106901742 A |   | 6/2017 |
|----|-------------|---|--------|
| CN | 206565948 U |   | 10/2017 |
| CN | 208481954 U | * | 2/2019 |
| CN | 208481954 U |   | 2/2019 |
| CN | 110368651 A |   | 10/2019 |

OTHER PUBLICATIONS

English-language machine translation of CN-208481954-U (Year: 2023).*

* cited by examiner

*Primary Examiner* — Andrey Shostak
(74) *Attorney, Agent, or Firm* — Cheng-Ju Chiang (57) ABSTRACT

A device for encouraging and guiding a spirometer user includes a housing, a main valve, a visual assembly, and a sound making assembly. The housing has a guiding channel, a first outlet channel, a second outlet channel, and an inlet channel. The main valve is disposed in a housing communicating with the guiding channel, the first outlet channel, the second outlet channel or the inlet channel and configured to regulate or control fluid flowing paths. The visual assembly includes a check valve in the second outlet channel, and at least one movable member. The sound making assembly includes a check valve and a sound maker. So, it can generate the visual and sound encouraging effects for learning how to use a spirometer correctly.

4 Claims, 11 Drawing Sheets

DEVICE FOR ENCOURAGING AND GUIDING A SPIROMETER USER AND ITS METHOD

BACKGROUND OF THE INVENTION

1. Field of the Invention

The invention relates to a device for encouraging and guiding a spirometer user and its method. This device includes a visual assembly and a sound making assembly. In which, a user may easily switch to a testing mode or a learning mode. It can generate both the visual and sound encouraging effects to encourage and guide the user. The structure is sample and easy to use.

2. Description of Related Art

A spirometer is a basic apparatus for measuring the volume of fluid (or air) inhaled and exhaled by the lungs. The spirometer is used especially for measuring forced vital capacity (briefly referred as FVC). In a spirometer test, a person takes a deep breath and then blows as hard as possible into a tube of the spirometer for lasting more than 6 seconds. Typically, the spirometer test fails due to the testing time lasting too long or incorrect inhale/exhale process. Specifically, the spirometer test fails if the person does not take a deep breath, blow as hard as possible or close the larynx.

Figure 8:
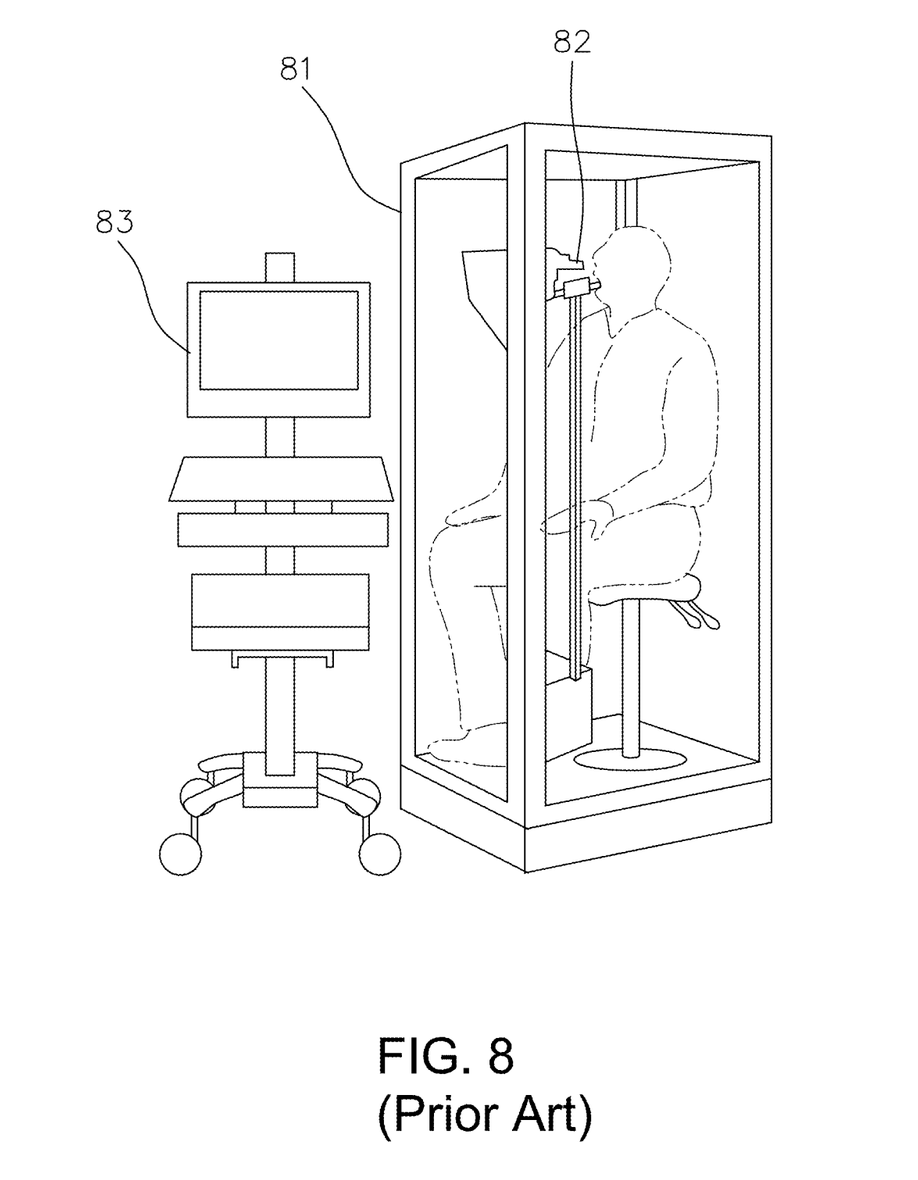
FIG. 8 is a perspective view of a conventional apparatus in condition of use.

As shown in FIG. 8, a conventional spirometer 82 is installed in a booth 81. A machine 83 is provided externally of the booth 81 and operatively connected to the spirometer 82. A person takes a deep breath and blows as hard as possible into a tube of the spirometer 82. A medical professional monitors a screen of the machine 83 in order to know the result.

Further, there is another simple-typed spirometer which is not installed in the booth 81. The machine 83 is and operatively connected to the spirometer 82. A medical professional is required to monitor the screen of the machine 83 in order to know the result.

A typical method of teaching a person to properly take a spirometer test involves showing a learning window (e.g., blowing a candle) on the screen of the machine. A person may learn how to take a breath and blow by watching the window. This method can teach a person how to breathe. But the person has to face the screen. In the test, the screen is turned to face a medical professional. The screen turning is a tedious task. Further, a person cannot learn how to breathe and blow by watching the screen. The medical professional is required to repeatedly explain the test procedure to the person and it is time consuming and inconvenient. Most importantly, a person cannot have a visually or audibly feedback during the process for learning how to breathe and blow correctly. The learning effect of this conventional spirometer is slow and quite limited.

Thus, the need for improvement still exists.

SUMMARY OF THE INVENTION

The invention has been made in an effort to solve the problems of the conventional art by providing a device for encouraging and guiding a spirometer user and its method.

To achieve above and other objects of the invention, the invention provides a device for encouraging and guiding a spirometer user comprising a housing including a guiding channel, a first outlet channel, a second outlet channel, and an inlet channel wherein the guiding channel communicates with one of the first outlet channel, the second outlet channel, and the inlet channel; and the second outlet channel includes at least one vent hole; a main valve disposed to communicate with the guiding channel, the first outlet channel, the second outlet channel or the inlet channel and configured to regulate, direct or control fluid flow through the guiding channel, the first outlet channel, the second outlet channel or the inlet channel; a visual assembly including a check valve disposed in the second outlet channel, and at least one movable member that being moveably disposed on the corresponding at least one vent hole; and a sound making assembly including a check valve disposed at an end of the inlet channel, and a sound maker;

wherein when the main valve is switched to force the guiding channel communicating with the first outlet channel and a fluid flowing through the guiding channel and further flowing to the first outlet channel through the main valve so as to conduct a spirometer test;

wherein when the main valve is switched to force the guiding channel communicating with the second outlet channel and a fluid flowing through the guiding channel, the fluid further flowing to the at least one vent hole through the main valve, the second outlet channel, and the check valve, thereby moving the at least one movable member up and down repeatedly to generate a visual encouraging effect; and wherein when the main valve is switched to force the guiding channel communicating with the inlet channel and a fluid flowing through the guiding channel, the fluid reversely flowing through the inlet channel and through the check valve, thereby the fluid flowing through the sound maker to generate a sound encouraging effect.

The invention further provides a method of using a spirometer comprising the steps of a preparing step, a spirometer testing step, and an encouraging and guiding step.

The above and other objects, features and advantages of the invention will become apparent from the following detailed description taken with the accompanying drawings.

DETAILED DESCRIPTION OF THE INVENTION

Referring to FIGS. 1A to 5B, this invention includes a device for encouraging and guiding a spirometer user. It mainly comprises a housing 10, a main valve 20, a visual assembly 30, and a sound making assembly 40.

Regarding this housing 10, it includes a guiding channel 11, a first outlet channel 12, a second outlet channel 13 and an inlet channel 14. The guiding channel 11 communicates with one of the first outlet channel 12, the second outlet channel 13 and the inlet channel 14. The second outlet channel 13 includes a plurality of vent holes 131 (three are shown).

About this main valve 20, it is disposed in the housing 10 to communicate with the guiding channel 11, the first outlet channel 12, the second outlet channel 13 or the inlet channel 14 for regulating, directing or controlling the flow of a fluid through the guiding channel 11, the first outlet channel 12, the second outlet channel 13 or the inlet channel 14.

Concerning this visual assembly 30, it includes a check valve 31 disposed in the second outlet channel 13, and a plurality of movable members 32 (three are shown). Each movable member 32 is moveably disposed on the corresponding vent hole 131. The movable member 32 is a light-weight ball (such as a ping pong ball or the like; that can be blown up easily).

The sound making assembly 40 includes a check valve 41 (such as one-way valve) disposed at an end of the inlet channel 14, and a sound maker 42.

When the main valve 20 is switched (or turned) to force the guiding channel 11 communicating with the first outlet channel 12 (see FIG. 2B) and a fluid (e.g., air) 90 flowing through the guiding channel 11 by exhaling, the fluid 90 flows to the first outlet channel 12 through the main valve 20 so as to conduct a spirometer test.

Figure 3:
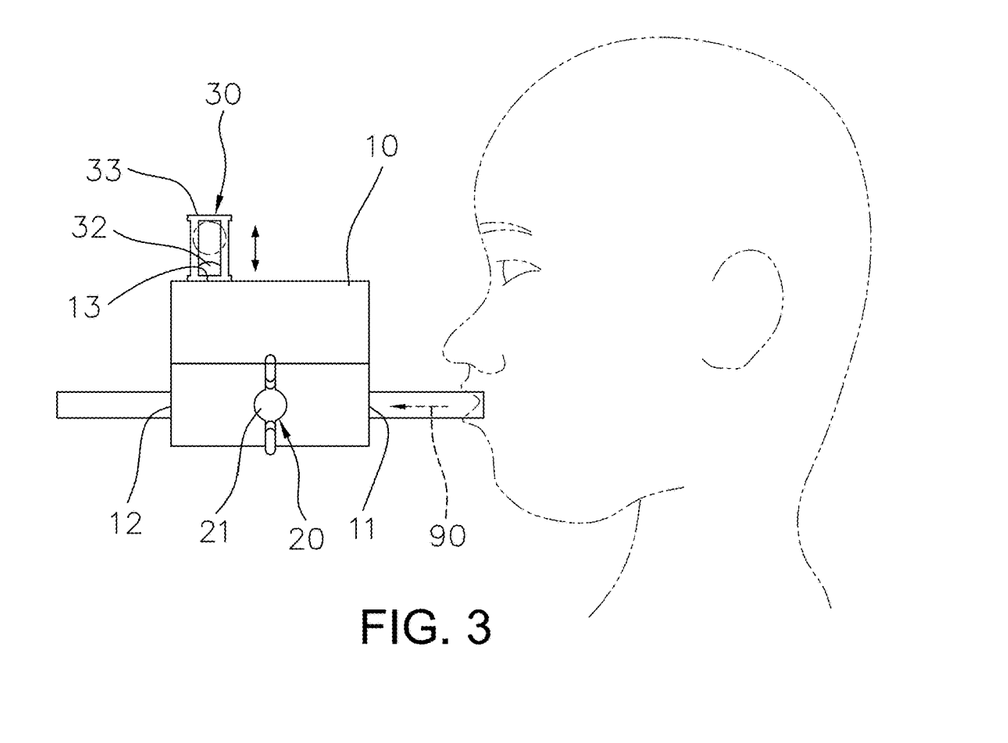
FIG. 3 is a perspective view of the apparatus of the second preferred embodiment of this invention.
Figure 4A:
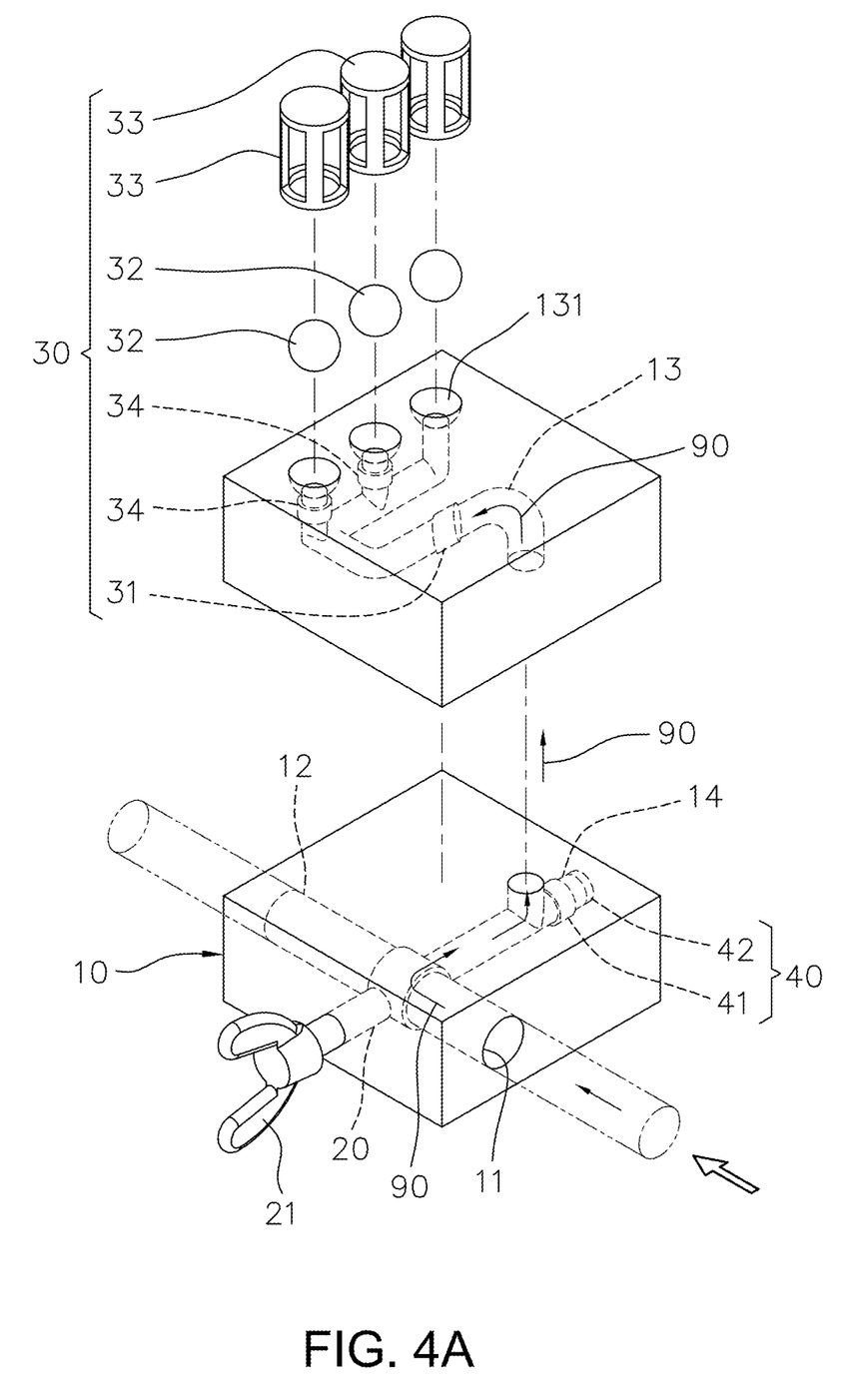
FIG. 4A is an exploded view of the apparatus of FIG. 3.
Figure 4B:
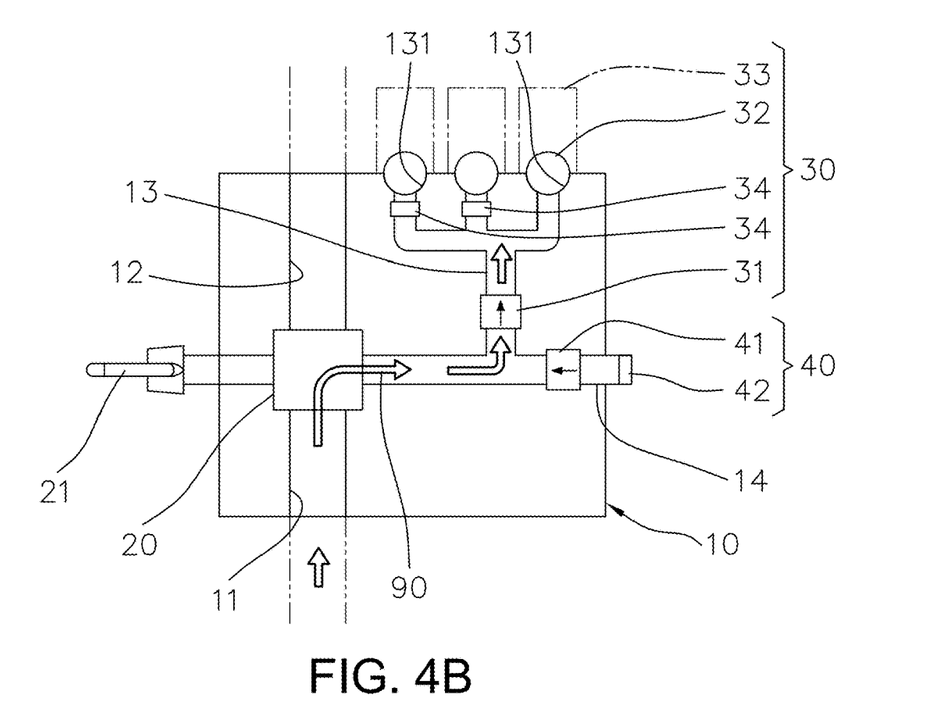
FIG. 4B schematically depicts a flow path of the assembled apparatus of FIG. 4A.

When the main valve 20 is switched to force the guiding channel 11 communicating with the second outlet channel 13 (see FIG. 4B) and a fluid 90 flows through the guiding channel 11 by exhaling (see FIG. 3), the fluid 90 flows to the vent holes 131 through the main valve 20, the second outlet channel 13, and the check valve 31 (see FIGS. 4A and 4B). Also, the movable members 32 move up and down repeatedly (see FIG. 4C). As a result, a visual encouraging effect is generated.

When the main valve 20 is switched to force the guiding channel 11 communicating with the inlet channel 14 (as well as a portion of the second outlet channel 13) and the fluid 90 flowing through the guiding channel 11 by inhaling (see FIGS. 5A and 5B), the fluid 90 reversely flows through the inlet channel 14 and through the check valve 41. The fluid 90 flowing through the sound maker 42 to generate a sound encouraging effect.

Practically, the main valve 20 includes a wing-shaped handle 21 extending from the housing 10. A user may turn the handle 21 to communicate the inlet channel 14 with the first outlet channel 12, the second outlet channel 13 or the inlet channel 14.

The visual assembly 30 may further comprise a plurality of limiters 33 (three are shown) on the housing 10 with the movable members 32 disposed therein respectively. The limiter 33 has a plurality of apertures for exiting fluid (or air). The movable member 32 may jump in the limiter 33 between a top of the limiter 33 and the vent hole 131.

The visual assembly 30 further comprises a plurality of valves 34. Each valve 34 is directly disposed below the vent hole 131. The valve 34 can control an opening or closing of the vent hole 131.

The sound maker 42 is implemented as a whistle or an element that is capable of making sound when the fluid 90 passes.

Figure 7:
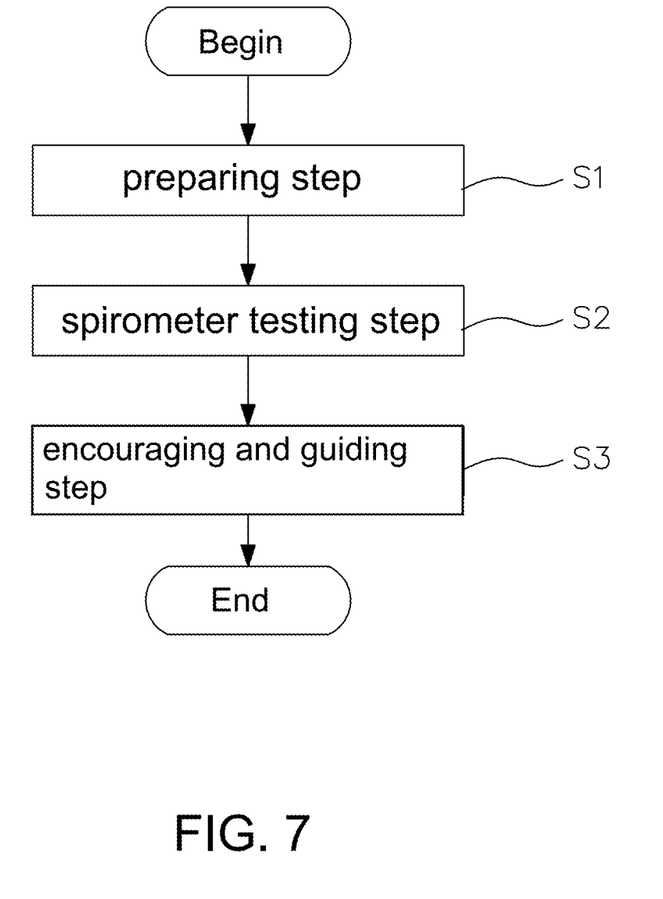
FIG. 7 is a flow chart of the method of this invention.

Referring to FIG. 7, a flow chart of a method for encouraging and guiding a spirometer user of this invention is illustrated. Also referring to FIGS. 1 to 5B, the method comprises the steps of:

[1] a preparing step S1: preparing a housing 10, a main valve 20, a visual assembly 30 and a sound making assembly 40. The housing 10 includes a guiding channel 11, a first outlet channel 12, a second outlet channel 13 and an inlet channel 14. The guiding channel 11 communicates with one of the first outlet channel 12, the second outlet channel 13 and the inlet channel 14. The second outlet channel 13 includes a plurality of vent holes 131. The main valve 20 is disposed in the housing 10 to communicate with the guiding channel 11, the first outlet channel 12, the second outlet channel 13 and the inlet channel 14 for regulating, directing or controlling the flow of a fluid through the guiding channel 11, the first outlet channel 12, the second outlet channel 13 and the inlet channel 14. The visual assembly 30 includes a check valve 31 disposed in the second outlet channel 13, and a plurality of movable members 32 each moveably disposed on the vent hole 131. The sound making assembly 40 includes a check valve 41 disposed at an end of the inlet channel 14, and a sound maker 42.

[2] a spirometer testing step S2: by switching the main valve 20 to communicate the guiding channel 11 with the first outlet channel 12 and the fluid (e.g., air) 90 flows through the guiding channel 11 by exhaling, the fluid 90 flows to the first outlet channel 12 through the main valve 20 so as to conduct a spirometer test; and

[3] an encouraging and guiding step S3: by switching the main valve 20 to communicate the guiding channel 11 with the second outlet channel 13 and the fluid flows through the guiding channel 11 by exhaling (see FIG. 3). The fluid 90 further flows to the vent holes 131 through the main valve 20, the second outlet channel 13, and the check valve 31 (see FIGS. 4A and 4B). Also, the movable members 32 move up and down repeatedly (see FIG. 4C). As a result, a visual encouraging effect is generated. By switching the main valve 20 to communicate the guiding channel 11 with the inlet channel 14 (as well as a portion of the second outlet channel 13) and the fluid 90 flows through the guiding channel 11 by inhaling (see FIGS. 5A and 5B). The fluid 90 reversely flows to the inlet channel 14 through the check valve 41. The fluid 90 flows through the sound maker 42 to generate a sound encouraging effect.

The main valve 20 includes a wing-shaped handle 21 extending from the housing A user may turn the handle 21 to communicate the inlet channel 14 with the first outlet channel 12, the second outlet channel 13 or the inlet channel 14.

The visual assembly 30 further comprises a plurality of limiters 33 (three are shown) on the housing 10 with the movable members 32 disposed therein respectively. The limiter 33 has a plurality of apertures (or openings) for exiting fluid 90 (or air). The movable member 32 may jump in the limiter 33 between a top of the limiter 33 and the vent hole 131.

The visual assembly 30 further comprises a plurality of valves 34 that are directly disposed to the corresponding vent hole 131. The valve 34 can control an opening or closing of the vent hole 131.

The sound maker 42 is implemented as a whistle or an element which is capable of making sound when the fluid 90 passes.

Figure 1A:
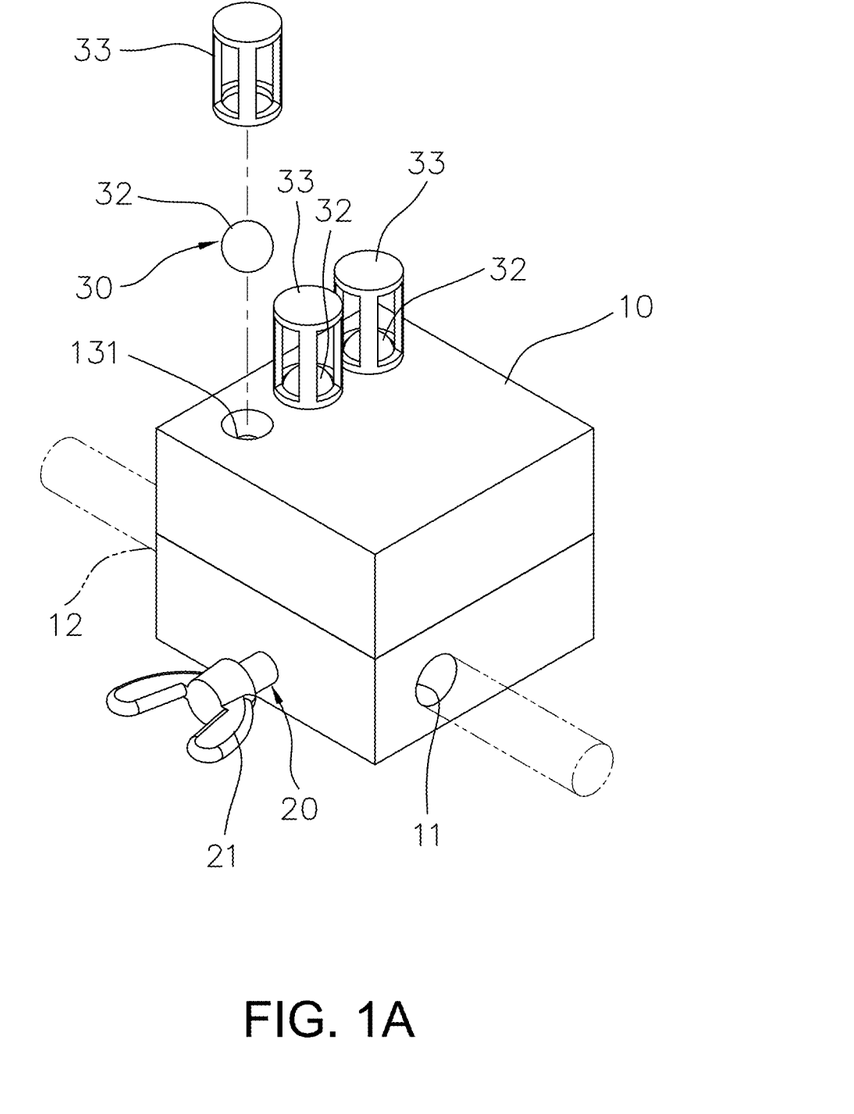
FIG. 1A is an exploded, perspective view of a spirometer of the invention.
Figure 1B:
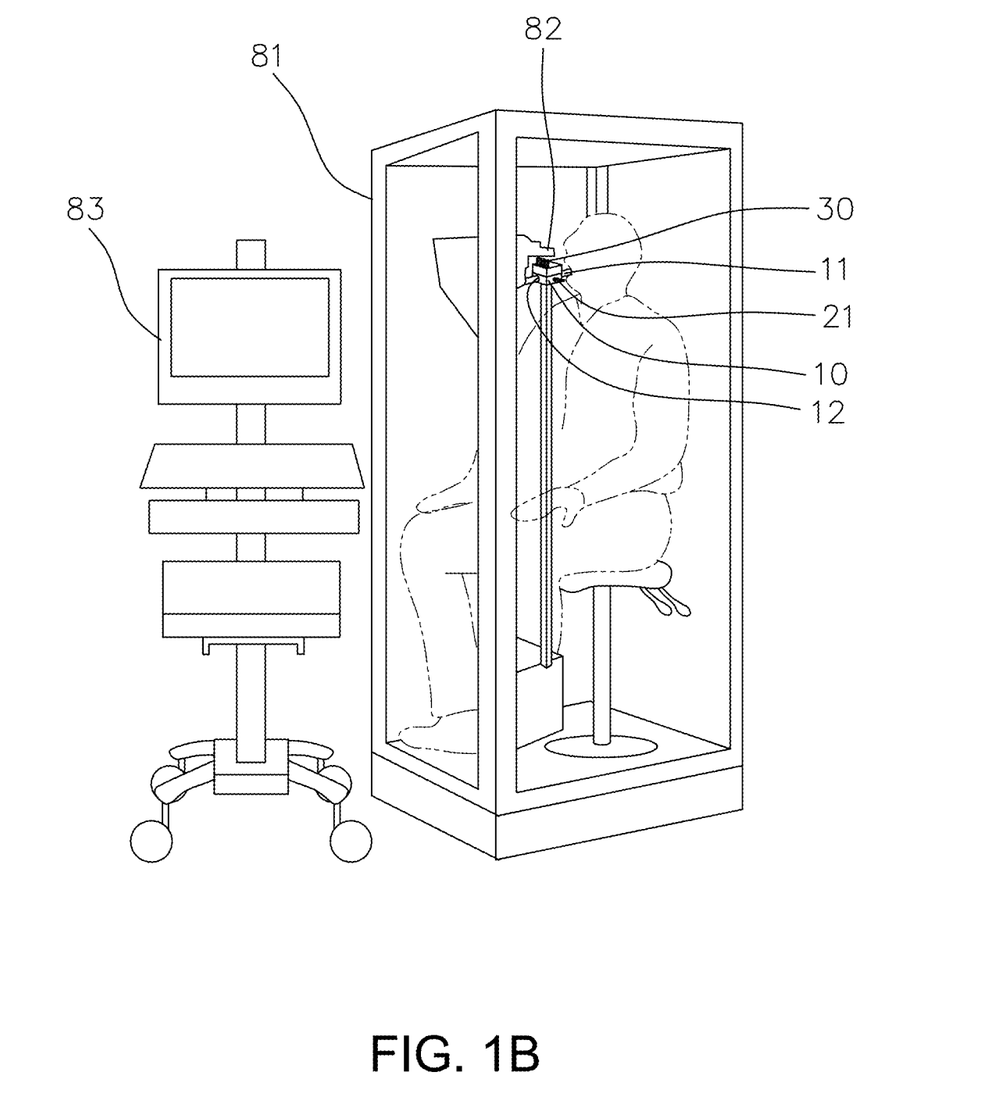
FIG. 1B is a perspective view showing the apparatus in condition of actual use.

The invention is directed to the spirometer test. As shown in FIG. 1B, the spirometer 82 is installed in a booth 81 by mounting on a support. A machine 83 is provided externally of the booth 81 and operatively connected to the first outlet channel 12. It is noted that the connection of the machine 83 to the spirometer 82 is not subject of the invention and is not discussed in detail for the sake of brevity.

The invention has two use modes as detailed below.

Figure 2A:
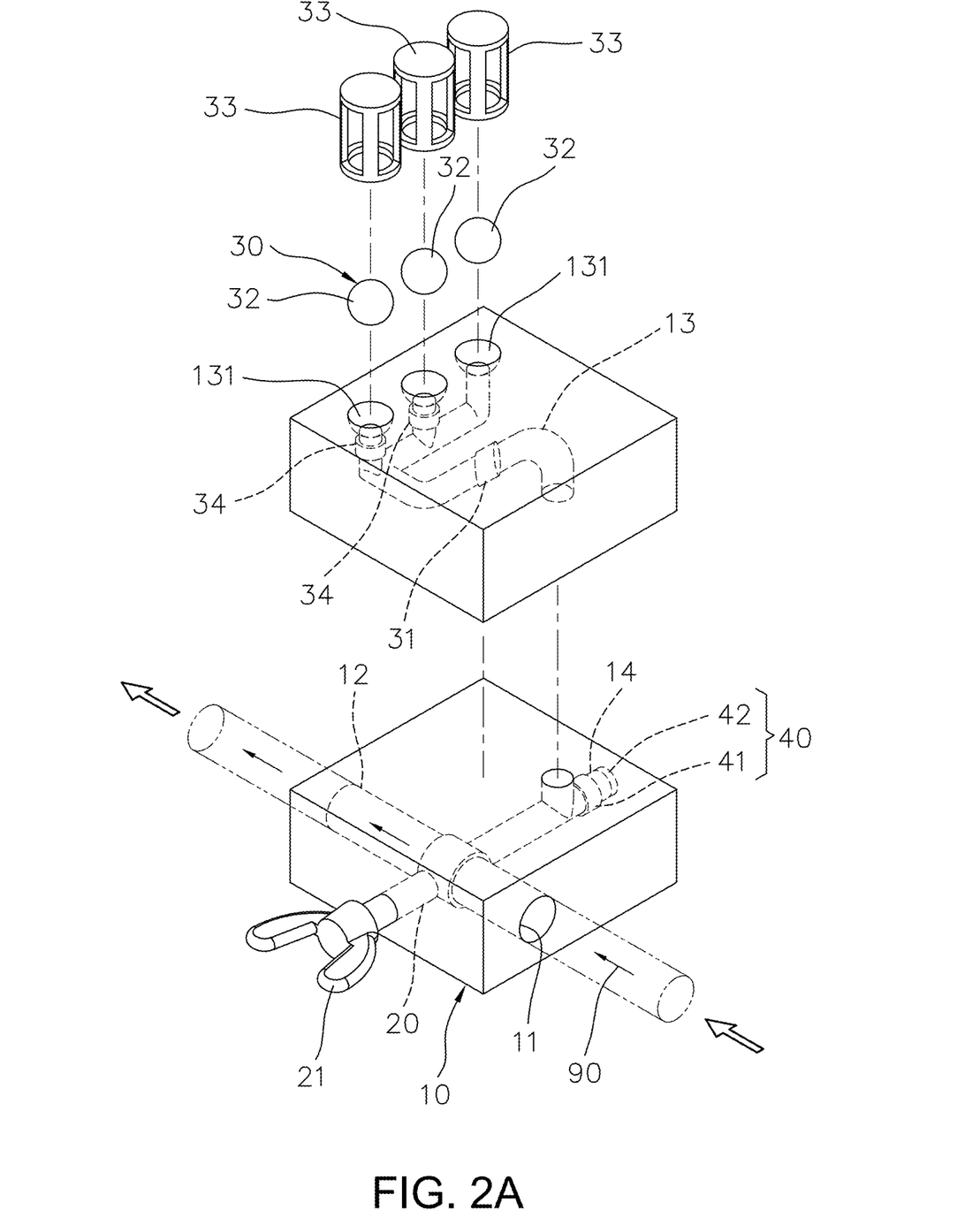
FIG. 2A is an exploded view of the first preferred embodiment of this invention.
Figure 2B:
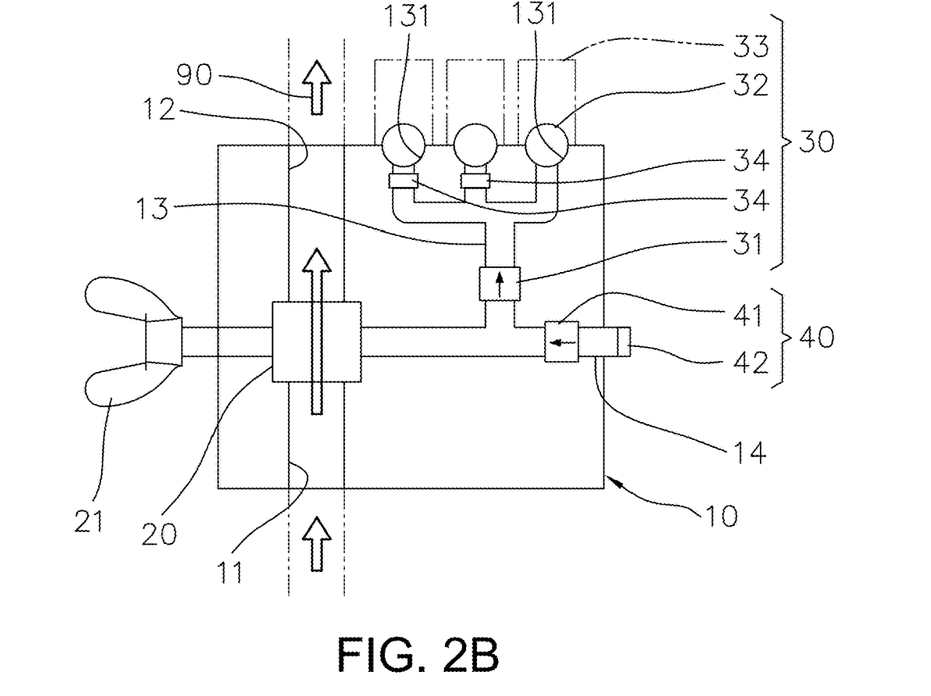
FIG. 2B schematically depicts a flow path of the assembled apparatus.

The first use mode is taking a spirometer test (see FIGS. 2A and 2B). A person takes a deep breath and blows as hard as possible into a tube of the spirometer 82. In detail, the main valve 20 is switched to communicate the guiding channel 11 with the first outlet channel 12, the person blows fluid 90 into the guiding channel 11. And in turn, fluid 90 flows to the spirometer 82 via the main valve 20 and the first outlet channel 12 so as to conduct the spirometer test.

In FIGS. 2B, the positions about the vent holes 131, the movable members 32, the valves 34, and the limiters 33 are slightly adjusted for better understanding. However, the actual spatial positions can be seen in FIG. 2A.

The second use mode is learning the spirometer test (with encouraging and guiding effects). For a beginner, it is possible that the beginner may not be able to successfully finish the first use mode. Thus, the invention provides visual/sound modes of learning the spirometer test as detailed below.

As shown in FIGS. 3, 4A and 4B, regarding the visual encouraging effect, the main valve 20 is switched to communicate the guiding channel 11 with the second outlet channel 13, the person blows fluid 90 into the guiding channel 11. The fluid 90 exits via the main valve 20, the second outlet channel 13, the check valves 31 and the vent holes 131. At the same time the movable members 32 repeatedly jump up and down randomly (see FIG. 4C), thereby generating a visual encouraging effect. It is also found that the harder the user blows, the higher the movable members 32 jump. Therefore, the person knows that he/she correctly blows the fluid 90 (or air).

Figure 4C:
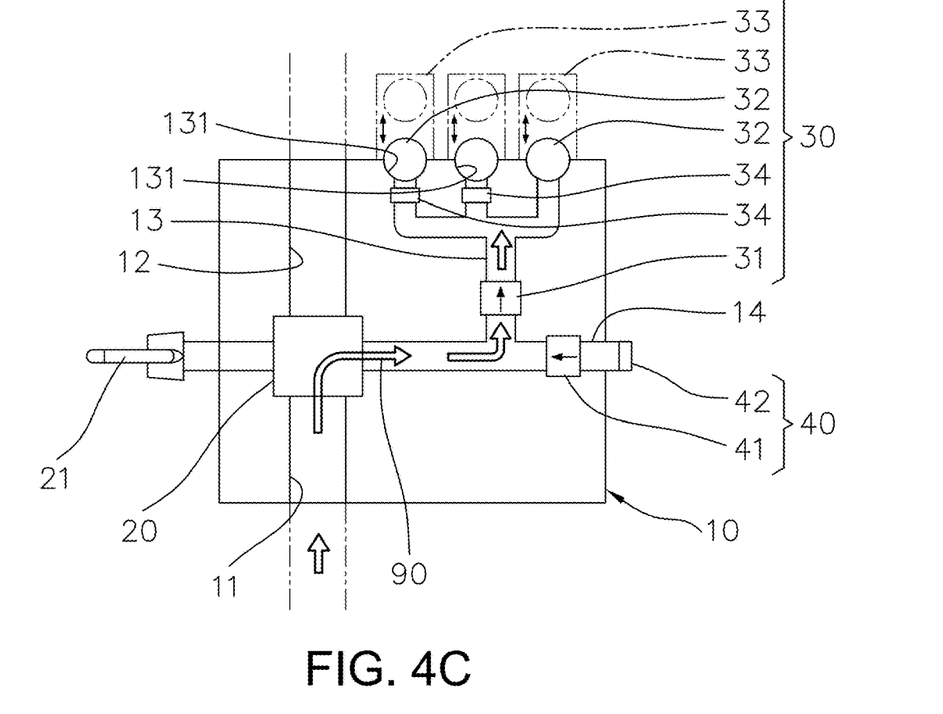
FIG. 4C schematically further depicts the flow path.

In FIGS. 4B and 4C, the positions about the vent holes 131, the movable members 32, the valves 34, and the limiters 33 are slightly adjusted for better understanding. However, the actual spatial positions can be seen in FIG. 4A.

Figure 5A:
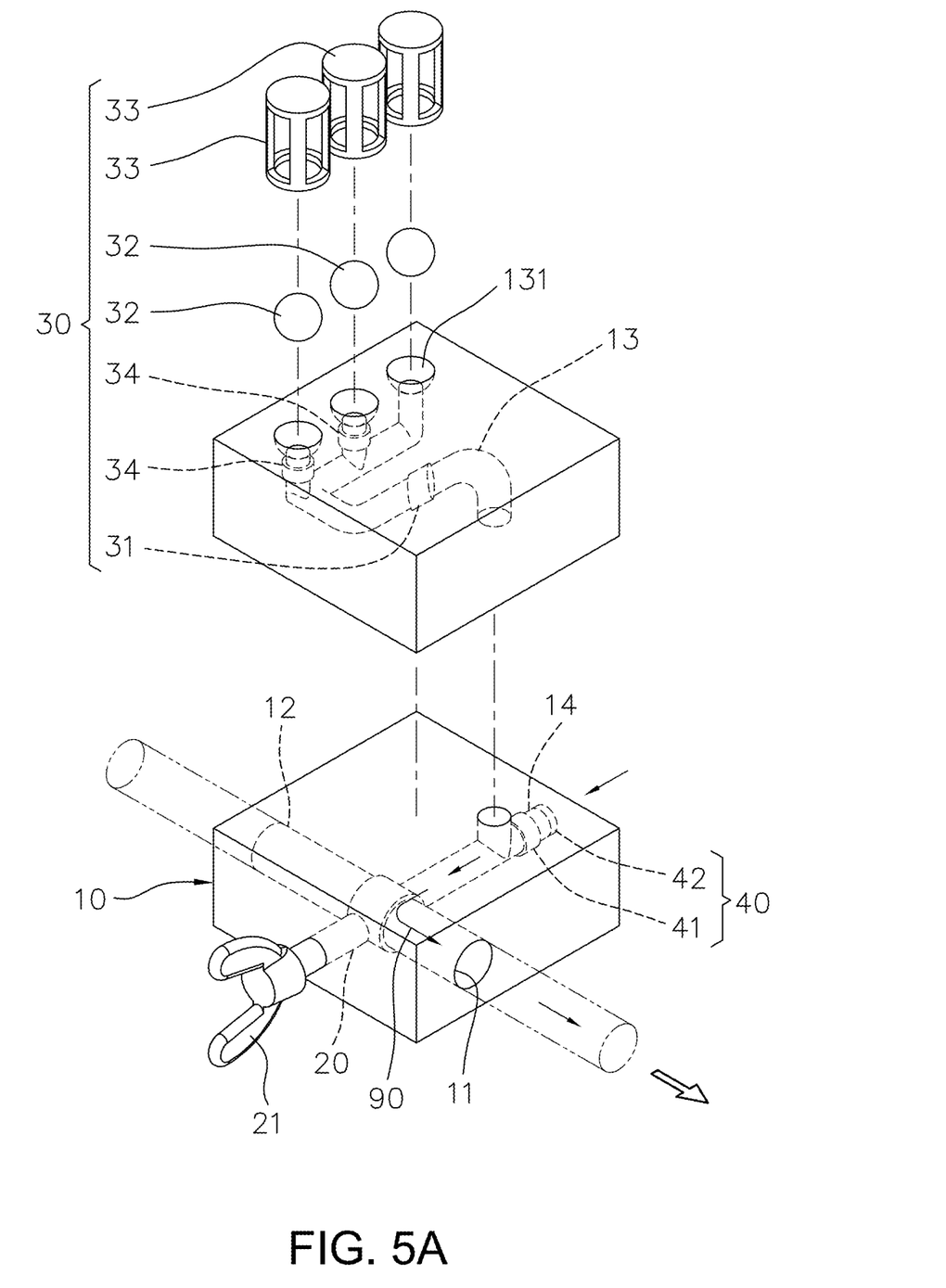
FIG. 5A is an exploded view of the apparatus of the third preferred embodiment of this invention.
Figure 5B:
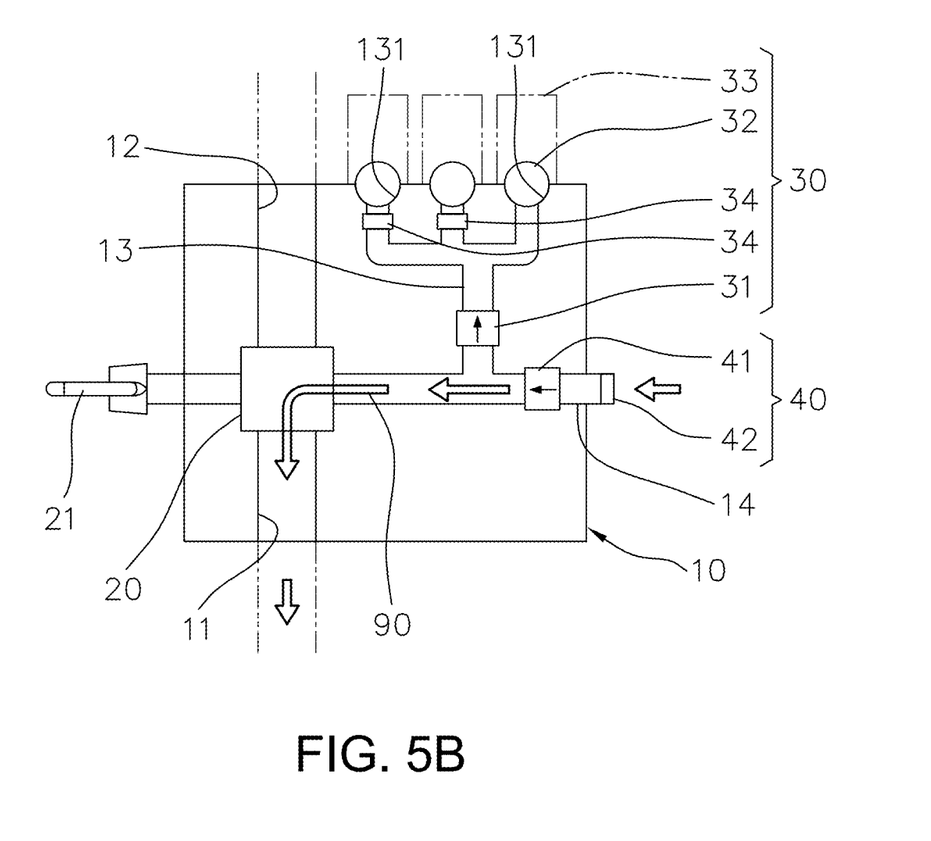
FIG. 5B schematically depicts a flow path of the assembled apparatus of FIG. 5A.

As shown in FIGS. 5A and 5B, regarding the sound encouraging effect, the main valve 20 is switched to communicate the guiding channel 11 (as well as a portion of the second outlet channel 13) with the inlet channel 14, the person inhales the fluid 90 into the guiding channel 11, and the fluid 90 reversely flows to the inlet channel 14 through the check valve 41. The fluid 90 flows through the sound maker 42 to generate a sound encouraging effect. It is also found that if the user inhales harder, the sound (whistle) lasts longer. Therefore, the person knows that he/she knows the difference between inhaling slightly and inhaling hard.

In FIGS. 5B, the positions about the vent holes 131, the movable members 32, the valves 34, and the limiters 33 are slightly adjusted for better understanding. However, the actual spatial positions can be seen in FIG. 5A.

Whether the blowing is hard or not is a subject of the person taking the test. The person may blow hard initially and lose steam thereafter. While a person may not be able to feel small fluid flow, the spirometer can detect it as long as the person blows. Thus, the spirometer can detect small respiratory symptom. But the result may be incorrect if the person does not blow continuously during the test. In detail, forced vital capacity (FVC) may be decreased. In case forced expiratory volume in one second ($FEV_1$) is unchanged, $FEV_1$/FVC increases. As such, it is impossible of evaluating any obstructive pulmonary disease. Therefore, a person taking the test is encouraged to exhale in $FEV_1$.

Details can be found in Table 1 below. Result volume of fluid (or air) inhaled and exhaled by the lungs is defined in which $FEV_{2-6}$ is defined as forced expiratory volume in 2-6 seconds. At the condition of air flow rate of 100 mL/sec, the more of the open vent holes 131 being open (as shown in FIG. 2A, from left to right one valve 34 disposed below the first vent hole 131, the other valve 34 disposed below the second vent hole 131 and the third vent hole 131 being always open as detailed in Table 1), the more significant of the visual encouraging effect.

TABLE 1

| Number of open vent holes | Total vent area (cm$^2$) | Accumulated volume (mL) | Opening or not |
|---|---|---|---|
| Open one vent hole | 0.785 | 392.5 | Always open |
| Open two vent holes | 1.570 | 785.0 | Open when ≥785 mL |
| Open three vent holes | 2.355 | 1177.5 | Open when ≥1177.5 mL |

Real $FEV_1$ is low for chronic obstructive pulmonary disease (COPD) or asthma. Real $FEV_1$ is low for limiting diseases such as pectus excavatum. Thus, result volume of air inhaled and exhaled by the lungs can be modified as below.

For ordinary people or people not aware of having COPD or limiting diseases (like pectus excavatum), estimated FVC—estimated $FEV_1$.

For people having symptom of COPD such as smoking or asthma, estimated FVC—0.8*estimated $FEV_1$.

For people having symptom of limiting diseases such as chest limiting disease, estimated FVC—0.8*estimated $FEV_1$.

Figure 6A:
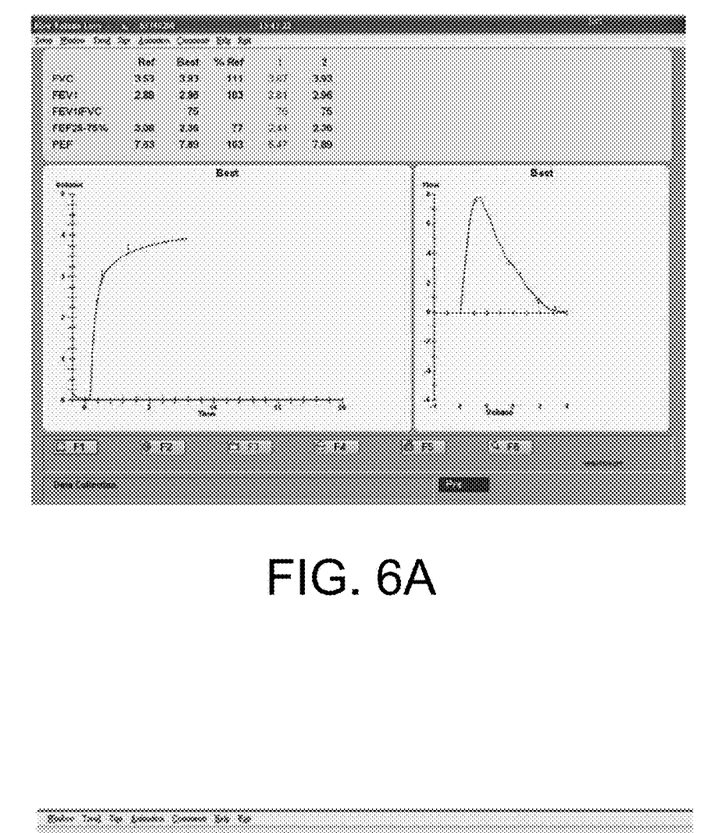
FIG. 6A is a chart of a first application of the invention.

In one example, radius of any vent hole 131 is labeled r and has a value of 0.5 cm, a patient taking the test, estimated FVC is 3.53 L and estimated $FEV_1$ is 2.88 L (see FIG. 6A), and result volume is 3.53−2.88=0.65 L=650 mL.

For training a person to blow fluid 90 in case two vent holes 131 (e.g., the first and third vent holes or the first and second vent holes) are open, the volume of air blown by the person is 0.97 L, the person can exhale for 6 seconds, and the movable members 32 can jump or spin.

Figure 6B:
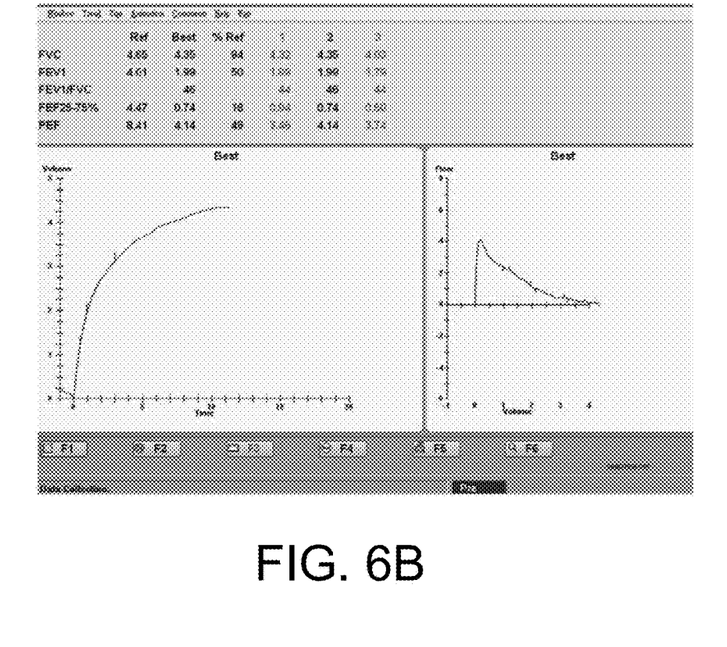
FIG. 6B is a chart of a second application of the invention.

For a person taking the test being a smoker, estimated FVC is 4.65 L and estimated $FEV_1$ is 4.01 L (see FIG. 6B), and result volume is 4.65−4.01*0.8=1.44 L=1440 mL.

For training a person to blow fluid 90 (or air) in case three vent holes 131 are open, the volume of air blown by the person is 2.36 L, the person can exhale for 6 seconds, and the movable members 32 can jump or spin.

The invention has the following advantages and benefits in comparison with the conventional art:

[1] The spirometer test and spirometer test learning modes can be easily switched. The main valve is disposed in the housing and can be operated to switch between the spirometer test mode and the spirometer test learning mode. In the spirometer test mode, a spirometer test is conducted. For people not familiar with the spirometer test and being subject to failure, it is possible of switching to the spirometer test learning mode so that the people can learn how to take a deep breath and blow (or inhale) as hard as possible using the spirometer. After has been familiar with the spirometer test, the people may take the spirometer test. In short, the spirometer test and spirometer test learning modes can be easily switched.

[2] The visual and sound encouraging effects aim to encourage people to take or learn the spirometer test. The person taking the spirometer test can see the movable members repeatedly jump by the upward flowing fluid (or air). Further, if the user blows harder, the movable members jump more strongly. Thus, the person knows that his or her blowing action is correct. When fluid flowing through the guiding channel, the fluid reversely flows to the inlet channel through the check valve, thereby flowing fluid through the sound maker to generate a sound encouraging effect. It is found that the user inhales harder, the sound (whistle) lasts longer. Therefore, the person knows that his or her blowing action is correct. In short, the visual and sound encouraging effects can encourage people to take or learn the spirometer test.

[3] The spirometer is easy to operate due to simple components. The spirometer is portable, i.e., not being fixed. The spirometer is especially suitable for people having experience of failing the spirometer test. In short, the person may learn how to take a spirometer test using the spirometer. After has been familiar with the spirometer test, the person may take the spirometer test. In short, the spirometer test is facilitated and the operation of the spirometer is made easy due to the simple components.

While the invention has been described in terms of configurations, those skilled in the art will recognize that the invention can be practiced with modifications within the spirit and scope of the appended claims.

What is claimed is:

1. A method for encouraging and guiding a spirometer user, comprising the steps of:
    a preparing step: preparing a housing, a main valve, a visual assembly, and a sound making assembly wherein the housing includes a guiding channel, a first outlet channel, a second outlet channel, and an inlet channel; the guiding channel communicates with one of the first outlet channel, the second outlet channel, and the inlet channel; the second outlet channel includes at least one vent hole; the main valve is disposed to communicate with the guiding channel, the first outlet channel, the second outlet channel or the inlet channel for regulating, directing or controlling fluid flow through the guiding channel, the first outlet channel, the second outlet channel or the inlet channel; the visual assembly includes a check valve disposed in the second outlet channel, and at least one movable member that is moveably disposed on the corresponding at least one vent hole; and the sound making assembly includes a check valve disposed at an end of the inlet channel, and a sound maker;
    a spirometer testing step: switching the main valve to communicate the guiding channel with the first outlet channel and said fluid flowing through the guiding channel by exhaling and said fluid further flowing to the first outlet channel through the main valve so as to conduct a spirometer test; and
    an encouraging and guiding step: switching said main valve to communicate the guiding channel with the second outlet channel and the fluid flowing through the guiding channel by exhaling, the fluid further flowing to the at least one vent hole through the main valve, the second outlet channel, and the check valve; and each movable member moves up and down repeatedly; and switching the main valve to communicate the guiding channel with the inlet channel and said fluid flowing through the channel by inhaling, said fluid further reversely flowing through the inlet channel and through the check valve, and said fluid flowing through the sound maker.

2. The method for encouraging and guiding a spirometer user of claim 1, wherein the main valve is disposed in the housing and includes a handle extending from the housing, the handle being configured to turn to communicate the inlet channel with the first outlet channel, the second outlet channel or the inlet channel.

3. The method for encouraging and guiding a spirometer user of claim 1, wherein the number of the at least one vent hole is more than one, the number of the at least one movable member is more than one, and each movable member is moveably disposed on the vent hole.

4. The method for encouraging and guiding a spirometer user of claim 3, wherein the visual assembly further comprises a plurality of limiters for exiting fluid and receiving the movable members respectively so that the movable member is configured to jump in the limiter between a top of the limiter and the vent hole; each of the limiters has a plurality of apertures; and a plurality of valves being directly disposed to corresponding vent holes, the valve being configured to control an opening or closing of the vent hole; and wherein the sound maker is a whistle or an element that is capable of making sound when fluid passes.

* * * * *